United States Patent [19]

Mertwoy

[11] 4,228,674
[45] Oct. 21, 1980

[54] APPARATUS FOR MEASURING ANTI-WEAR PROPERTIES OF PRESSURIZED LIQUIDS

[75] Inventor: Abraham Mertwoy, Dresher, Pa.

[73] Assignee: The United States of America as represented by the Secretary of the Army, Washington, D.C.

[21] Appl. No.: 44,898

[22] Filed: Jun. 4, 1979

[51] Int. Cl.³ .................. G01N 3/56; G01N 19/02
[52] U.S. Cl. ............................................... 73/10
[58] Field of Search ............................. 73/10, 9, 64

[56] References Cited

U.S. PATENT DOCUMENTS

| | | | |
|---|---|---|---|
| 2,019,948 | 11/1935 | Boerlage | 73/10 |
| 2,370,606 | 2/1945 | Morgan et al. | 73/10 |
| 3,045,471 | 7/1962 | Chapman et al. | 73/10 |
| 3,302,447 | 2/1967 | Mertway et al. | 73/10 |
| 3,939,690 | 2/1976 | Kuss et al. | 73/9 |

FOREIGN PATENT DOCUMENTS 124199 9/1959 U.S.S.R. ......................................... 73/10

Primary Examiner—Gerald Goldberg
Assistant Examiner—Joseph W. Roskos
Attorney, Agent, or Firm—Nathan Edelberg; Robert P. Gibson; Max Yarmovsky

[57] ABSTRACT

A testing device for determining the lubrication properties of hydraulic fluids under elevated pressures and temperatures comprises a pressure-tight housing defining a central cavity including a continuous passageway for the fluid, a chuck assembly located within the cavity which holds a plurality of test balls in fixed position, a rotatable support structure securing an upper ball in centrally disposed contact with the test balls, and a screw-threaded adjustment adapted to move the chuck assembly to apply pressure between the test balls and the upper ball. The present testing device is of simple and inexpensive construction and reduced size, and provides data respecting the test fluids which accurately reflects actual working conditions.

9 Claims, 2 Drawing Figures

APPARATUS FOR MEASURING ANTI-WEAR PROPERTIES OF PRESSURIZED LIQUIDS

GOVERNMENTAL INTEREST

The invention described herein may be manufactured, used and licensed by or for the Government for governmental purposes without payment to me of any royalties thereon.

BACKGROUND OF THE INVENTION

The present invention relates to the area of testing devices, and specifically to an apparatus for determining the controlled effect of temperature and pressure on the lubrication properties of hydraulic fluids.

Until rencently, prior art laboratory test bench devices endeavoring to measure the lubricity or anti-wear properties of hydrulic fluids, have been performed under ambient conditions. Employing a full scale mock-up of the apparatus with the particular fluid medium under consideration, in an attempt to simulate actual operating conditions, is costly. The mock-up tests are conducted for a given period of time at predetermined temperature and pressure levels, after which the entire assembly must be dismantled and the components examined for wear and weight loss and then usually replaced.

One of the drawbacks of a full scale mock-up is that it requires a large quantity of fluid, often greatly in excess of the quantities available as in the case of experimental fluids. Additionally, certain uncontrollable variables may be introduced, such as variations in composition between similar components of the mock-up, and variations in tolerance between the rubbing and sliding components contained and of the same components therein.

PRIOR ART STATEMENT

U.S. Pat. No. 3,302,447 of Mertwoy et al discloses an apparatus for the purpose of testing the lubricity of hydraulic fluids which comprises a chamber containing a quantity of fluid placed under pressure and surrounding a rotatable cup retaining free test balls against which a fourth ball is located in a stationary holder. The lubricity of the surrounding fluid is determined by examination of the fluid and the wear of the three test balls at the points of contact with the fourth ball.

The above described patented apparatus possesses certain limitations principally resulting from its design. Specifically, the load placed upon the test balls is varied by the placement of lead weights around a shaft and on top of the ball assembly, all of which is fully immersed in the fluid being tested. Through continued usage it was observed that the precise loads applied to the test balls could not accurately be determined, as the surrounding fluid exerted a buoyancy effect on the immersed weights. Also, the weights were constructed of lead, and lead particles were found in the test fluids which tended to contaminate them. Further, the size requirements of the device were such that it was still necessary to prepare relatively large quantities of fluid to be able to conduct a series of tests of the same fluid at different pressurs and temperatures. Lastly, the test fluid tended to fill a magnetic drive, and in the instance where the test fluid was viscous fluid, a significant drag was imposed on the magnetic drive, which made the operation of the testing device more difficult.

The present invention overcomes the aforementioned problems of the prior art devices.

SUMMARY OF THE INVENTION

A device for testing the lubricity of fluids is disclosed which comprises a housing open at one end having a cavity therein including a continuous passageway for the fluid, and a cover removably mounted on the housing in pressure-tight engagement with the open end. A plurality of test balls are held stationary within the housing and a upper ball is rotatably mounted in contact with each of the test balls. A chuck assembly is disposed within the cavity to fixedly retain the test balls and means for rotatably supporting the upper ball centrally of the test balls is also included. Pressure between the test balls and the upper ball is applied by means associated with the chuck assembly, and rotation of the upper ball in contact with the stationary test balls is provided by a rotation means associated with the upper ball supporting means.

The present device is characterized by simplicity of design and operation, and reliability of test results. Specifically, controlled loads up to 100 kilograms may be applied to the rubbing surfaces of the balls without the inaccuracy caused by the buoyancy effect of the fluid. The upper ball is rotated by a magnetic drive which is surrounded by fluid of low viscosity to reduce or eliminate drag upon the rotation of the upper ball rotation means. The device is designed to withstand fluid pressures of up to 100,000 psi with a reduced quantity of fluid which may be as little as 400 milliliters.

Accordingly, it is a principal object of the present invention to provide a fluid testing device for the accurate measurement of the effects of elevated load temperature and fluid pressure of the lubricity of experimental fluids.

It is a further object of the present invention to provide a testing device as aforesaid which is of reduced size and therefore requires reduced amounts of fluid for testing.

It is a yet further object of the present invention to provide a testing device as aforesaid which substantially reduces contamination of the fluid being tested.

It is a still further object of the present invention to provide a device as aforesaid wherein test results are faithfully attributable to fluid pressure parameters.

Other objects and advantages will become apparent to those skilled in the art from a review of the ensuing description which proceeds with reference to the following accompanying drawings.

DETAILED DESCRIPTION OF THE PREFERRED EMBODIMENT

Figure 1:
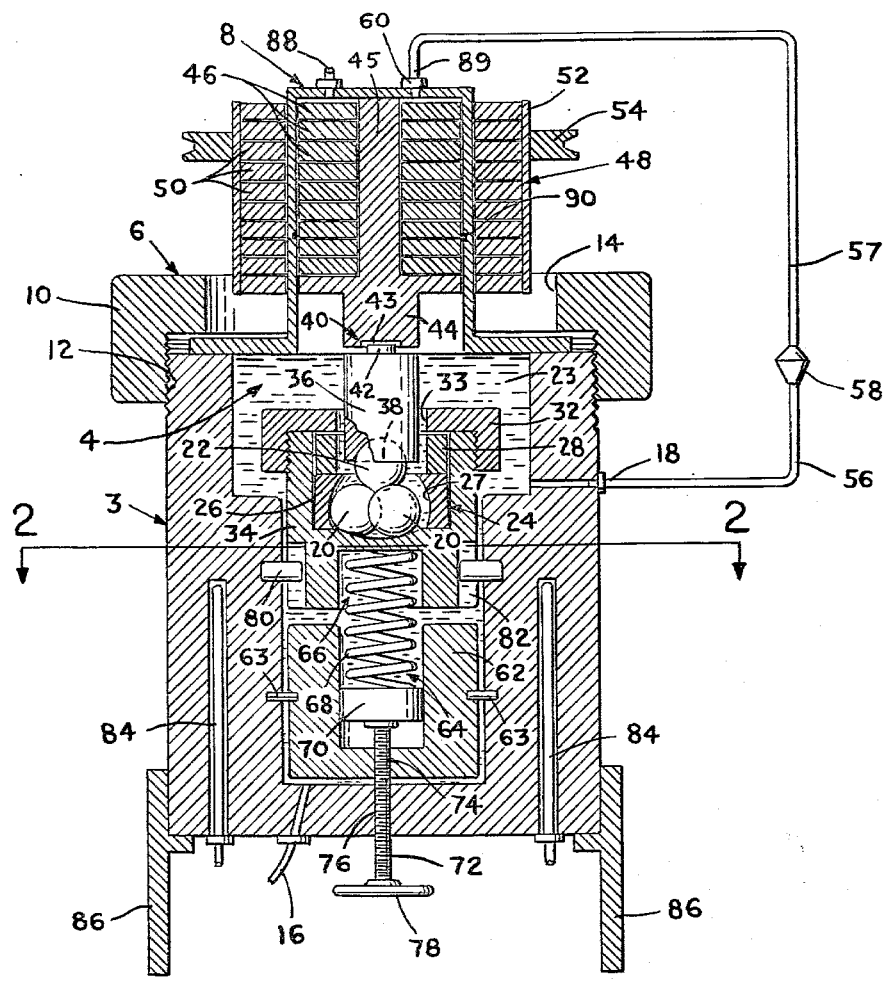
FIG. 1 is a partial diametral cross-sectional schematic view illustrating the present invention.

Referring to FIG. 1, the testing device of the present invention comprises a housing 3 open at one end and defining inside a cavity 4 which provides a continuous passageway for the hydraulic fluid to be tested. A cover assembly 6 comprises a lid 9 held in fluid-tight engagement with the open end of housing 3 by an internally threaded lock nut 10 adapted to mate with corresponding threads 12 provided on housing 3. Lock nut 10 has an opening 14 to permit the protrusion of lid 8, which is associated with a rotating means discussed in greater detail below.

A fluid inlet 16 and a fluid outlet 18 are each connected to cavity 4. Both inlet 16 and outlet 18 are operatively provided with either caps or valves to assure that fluid pressure is maintained within the housing 3. Pressure may be applied to the test fluid by a means not shown such as a hand pump, or a motorized pump.

The present testing device attempts to determine the properties of a lubricating fluid 23 under actual working conditions by measuring the scar diameters produced on test balls 20 by upper ball 22. Upper ball 22 is rotated while both the test balls 20 and the upper ball 22 are immersed in the lubricating fluid being tested. The rotation of the upper ball 22 against the test balls 20 tends to pull the lubricating fluid 23 between the mating surfaces of the test balls 20 and upper ball 23. This type of test is known in the art as the "Four Ball Wear Test".

In accordance with the present invention, test balls 20 are maintained stationary within housing 3, and upper ball 22 is centrally disposed and rotatably mounted thereabove. Test balls 20 are retained within a chuck assembly 24 which is preferably cylindrical in shape and is dished out to centrally locate test balls 20. A primary bearing 26 has an internal arcuate surface 27 which is adapted to position test balls 20 in axial alignment with ball 22. Bearing 26 is held in position by a washer 28. A centering clamp 32 similar to lock nut 10 is provided and threadedly engages the body 34 of chuck assembly 24 to retain test balls 20 securely positioned by bearing 26 and washer 28. The chuck assembly 24 maintains the test balls 20 in stationary position during the operation of the device.

Referring further to FIG. 1, upper ball 22 is maintained in axial alignment and in contact with test balls 20 by a rotatable supporting means comprising a collet 36 having at one end a hemispherical depression 38. Collet 36 may be provided with an appropriate locking nut or chuck for holding upper ball 22, as is well known in the art.

The central orifice 33 of centering clamp 32 allows collet 36 to intrude therethrough and permit contact to be made with test balls 20. Upper ball 22 is rotated by a rotating means comprising magnetic assembly 40 which removably engages the upper end of collet 36 and translates rotational movement through mating depression 43 to projection 42 on collet 36. Assembly 40 comprises support spindle 44 which has a reduced section 45 at the upper portion thereof for the placement thereon of disc-like magnetic plates 46 which give spindle 44 the appearance of an armature. Lid 8 projects upward to enclose spindle 44. Spindle 44 is contained within the cavity 4 defined by housing 3. Rotational force is translated to spindle 44 by means of annularly positioned outer magnetic armature 48 which comprises a plurality of magnetic plates 50 retained by an annular closure 52. Rotational movement is provided by a motor, not shown, which is connected by a belt drive to a pulley 54 which is mounted annularly on closure 52. The rotation means is adapted to rotate upper ball 22 at speeds of up to 1800 r.p.m. In a preferred embodiment, the motor employed to drive the present device should be capable of rotating at speeds of 600, 1200 and 1800 r.p.m. to enable tests to proceed at these differing rates of rotation.

Spindle 44 is in contact with the test fluid 23 of cavity 4. In accordance with the present invention the fluid entering the annular area between magnetic plates 46 and the interior surfaces of lid 8 is of controlled amount and viscosity. The fluid exiting outlet 18 is directed through a conduit 56 to a first side of diaphragm 58. The other side of diaphragm 58 communicates with a conduit 57 which is connected to lid entry port 60. Diaphragm 58 permits the fluid pressure of cavity 4 to be transmitted to the fluid of selected viscosity in the annular space between the magnetic plates 46 and the lid 8.

The present testing device also includes means associated with chuck assembly 24 for applying pressure between test balls 20 and upper ball 22. Referring again to FIG. 1, the pressure application means comprises an adjustable calibrated spring assembly adapted to urge test balls 20 into pressured contact with upper ball 22. The calibrated spring assembly comprises a cup-shaped sleeve 62 axially located in cavity 4 below chuck assembly 24 and spaced apart therefrom. It should be noted that both chuck assembly 24 and sleeve 62 are so disposed in cavity 4 as to define a space between their outer surfaces and the inner surface of cavity 4 to serve as the aforementioned continuous fluid passageway. Thus, as can be seen in FIG. 1, fluid entering through inlet 16 can circulate around cup-shaped sleeve 62 and chuck assembly 24 so that substantially all of the working components of the present testing device will be immersed in test fluid 23. Cup-shaped sleeve 62 is pinned by pins 63 to housing 3 to prevent rotation between the two members.

Referring further to FIG. 1, sleeve 62 contains a chamber 64 therein which opens in the direction of chuck assembly 24 and resides in axial alignment with a pocket 66 provided in the adjacent end of chuck assembly 24. Chamber 64 and pocket 66 are preferably cylindrical in shape and of similar diameter, as they cooperate to house a compressible coil spring 68 which is disposed with its axis of compression in alignment therewith. Chuck assembly 24 is free for axial reciprocation to and from upper ball 22. Spring 68 is operatively disposed within pocket 66 and is adapted to exert compressive force upon chuck assembly 24.

The spring assembly of the present invention includes a compression adjustment means comprising a piston 70 adapted for fluid-tight reciprocation within chamber 64 and in abutment with spring 68. The position of piston 70 is incrementally adjusted by the rotation of screw 72 which is threadedly retained within appropriate threaded openings 76 and 74 provided, respectively, in the bottom walls of sleeve 62 and housing 3. Screw 72 projects outward from housing 3 and terminates in an adjustment means comprising wheel 78 which is provided to control the travel of screw 72. Though not shown, screw 72 may be appropriately calibrated to indicate the amount of force exerted by a given increment of travel. The exact range of loads that may be applied by the present compression adjustment means is dependent upon the force rating of the spring 68, and accordingly, a spring may be appropriately selected which exhibits a range of forces which are desirable for the purposes of testing fluid with the present device. In a preferred embodiment, the present testing device may be operated with applied loads ranging up to 100 kilograms.

Figure 2:
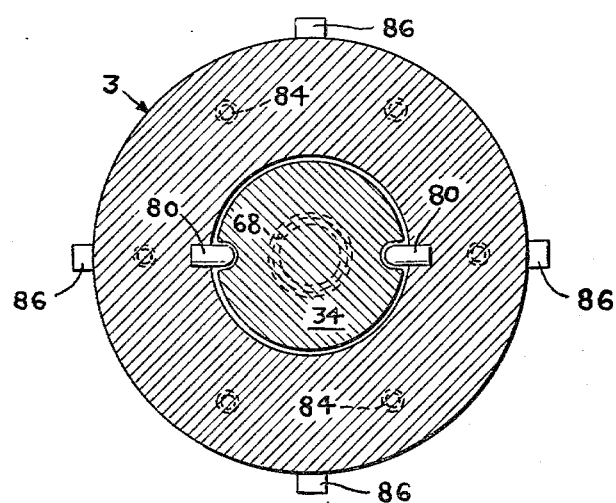
FIG. 2 is a top sectional partial cut-away view taken through line 2—2 of FIG. 1 further illustrating the present invention.

In operation, a plurality of test balls 20 are loaded into chuck assembly 24 which is then secured by the application of centering clamp 32. Assembly 24 is then loaded into cavity 4 as shown. As noted earlier, assembly 24, containing test balls 20 must not move during the operation of the present testing device. Thus, as illustrated in FIGS. 1 and 2, chuck assembly 24 may be held stationary within cavity 4 by the provision of cooperating pins 80 which are movably lodged within the inside wall of housing 3 and project into cooperation with mating slots 82 provided on the outer surface of assembly 24. Pins 80 are removable in the event that it should become necessary to remove sleeve 62 from cavity 4. Though the invention as illustrated employs removable pins, it is to be understood that alternate means may be employed to prevent the movement of assembly 24. For example, slots could be provided in the inside wall of housing 3 adapted to mate with projecting ridges provided on the outer surface of assembly 24. Thus, the foregoing description is presented for purposes of illustration and not limitation.

After assembly 24 is lowered into position as shown, collet 36 containing upper ball 22 is placed in position within the space provided by centering clamp 32, and supporting spindle 44 is lowered into linked abutment with collet 36. Lid 8 is placed over spindle 44 and is brought into fluid-tight engagement with housing 3 by the application and tightening of lock nut 10. In this regard, fluid-tight engagement can be assured by the provision of a gasket, not shown, between the abutting surfaces of lid 8 and housing 3. Where employed, gaskets may be prepared from well known organic resinous materials comprising natural and synthetic rubbers adapted to withstand the fluid pressures contemplated in the operation of the present device.

After the securement of lid 8, magnetic armature 48, including pulley 54 is mounted annularly thereon and mechanically linked to a source of rotational movement, not shown. After the sealing of the device is completed as described, spring 68 is adjusted by screw 72 in accordance with desired loading conditions, and the test fluid is then introduced by a pump, not shown, into fluid inlet 16. Fluid 23 enters the passageways surrounding the spring assembly, the balls 20 and 22 and their respective supporting assemblies. A pressure metering device, not shown, may be attached to the fluid conduit leading to inlet 16 to monitor the pressure on the test fluid after the passageways of the testing device are filled. A fluid of selected viscosity is introduced via inlet port 88, which is thereafter sealed. The selected viscosity fluid 89 partially fills the annular space intermediate magnets 46 and lid 8 and the conduit 57. The selected viscosity fluid 89 is prevented from mixing with test fluid 23 by seals 90 operatively positioned in the interior walls of lid 8. Diaphragm 58 is used to equalize pressure and separate fluids 23 and 89. Rotational force is then applied to pulley 54 to commence the rotation of ball 22. As noted earlier, the magnetic drive of the present invention is adapted to operate at rates of rotation of up to 1800 r.p.m.

The present device is capable of heating the test fluid 23 to a temperature of up to 400° F., by the application of external heat to the housing 3. In a preferred embodiment, and with reference to FIGS. 1 and 2, a plurality of heating elements 84 may be provided in annular disposition within housing 3 surrounding the portion of cavity 4 that contains sleeve 62 and chuck assembly 24. The exact number of heating elements 84 may vary within the skill of the art and the present invention is not limited to any particular number or disposition.

The present testing device may be mounted in any convenient manner in the upright position, shown in FIG. 1, by placement in a vice or the like. As illustrated in FIG. 1, the device may be conventionally supported by a set of legs 86.

The device of the present invention is compact in construction, and requires no more than about 400 milliliters of test fluid per test run. Test fluid is thus conserved, and a greater number of test runs can be conducted at various temperatures and pressures to determine the full range of properties of a given test fluid.

The present testing device is preferably constructed from materials capable of withstanding the temperatures and pressures contemplated, and, in a preferred embodiment, may be constructed from materials having high temperature stability and yield strengths ranging from 30–45,000 psi. Exemplary materials comprise wrought stainless steels having a composition of 18–20% chromium, 8–12% nickel, 0.03–0.08% carbon, 2.0% manganese, 1.0% silicon, 0.045% phosphorus, 0.030% sulfur and the remainder iron. These materials are known in the art as "type 304" stainless steel. A chromium-molybdenum alloy of suitable characteristics may likewise be employed.

It is to be understood that the invention is not limited to the illustrations described and shown herein, which are deemed to be merely illustrative of the best modes of carrying out the invention, and which are suitable of modification of form, size, arrangement of parts and details of operation. The invention rather is intended to encompass all such modifications which are within the spirit and scope and defined by the claims.

What is claimed is:

1. A testing device for determining the lubricity or anti-wear resistance characteristics of hydraulic fluids under elevated fluid pressures and temperatures, comprising:

a housing having an open end and a cavity therein including a continuous passageway for said fluids;

a cover removably mounted on said housing in pressure-tight engagement with said open end;

a fluid inlet and a fluid outlet, said fluid inlet connected with said continuous passageway to permit the flow of pressurized fluids in said housing;

a plurality of test balls held stationary within said housing;

an upper ball rotatably mounted in contact with each of said test balls;

a chuck assembly disposed within said cavity adapted to fixedly retain said test balls and to axially reciprocate toward said upper ball;

means for rotatably supporting said upper ball in axial alignment within said test balls;

means associated with said chuck assembly for applying pressure between said test balls and said upper ball which includes;

and adjustable calibrated spring assembly communicating with said chuck assembly and adapted to urge said test balls into pressured contact with said upper ball; and means associated with said upper ball supporting means for rotating said upper ball in contact with said test balls.

2. The testing device of claim 1 wherein said spring assembly comprises a sleeve located in said cavity below said chuck assembly and defining a chamber opening toward said test balls, a pocket defined in said chuck assembly opening toward said sleeve and in axial alignment with said chamber, a compressible coil spring extending from said chamber to said pocket with its axis of compression aligned therewith, and a compression adjustment means located within said chamber in axially aligned contact with said spring, said adjustment means adapted for incremental axial movement to exert a measured amount of compressibe force upon said spring, which force is spplied by said spring to said chuck assembly.

3. The testing device of claim 2 wherein said compression adjustment means comprises a piston adapted for fluid-tight reciprocation within said chamber in contact with said spring, an adjustment screw associated in alignment with said piston, said screw residing in aligned, fluid-tight, threaded engagement with threaded openings located, respectively, in said sleeve and said housing, and projecting exteriorly of said housing, and a rotating means for said screw located at the free end thereof for adjusting the travel and position of said piston.

4. The testing device of claim 1 wherein said upper ball supporting means comprises a cylindrical collet defining a hemispherical cavity to retain said upper ball and a magnetic drive disengageably mechanically linked to said collet to promote the rotation thereof.

5. The testing device of claim 4 wherein said magnetic drive comprises an inner, rotatable magnetic spindle, an outer rotatable magnetic armature located in annular displacement from said spindle, said spindle and said armature are independently rotatable and the rotation of said armature promotes the like rotation of said spindle, and a cylindrically outwardly distended lid defined by said cover is disposed between said spindle and said armature to retain said spindle within said cavity.

6. The testing device of claim 5 further including a rotatable pulley disposed in annular attachment to the outer circumference of said armature and adapted to receive and translate rotational motion from an external source thereof.

7. The testing device of claim 6 further including means for the controlled introduction of fluid to said spindle comprising an inlet port provided in said lid, said inlet port in fluid communication with a fluid conduit connected to said fluid outlet, said conduit provided along its length with a means for the regulation of the pressure of said fluid.

8. The testing device of claim 1 further including heating means disposed in said housing for the application of heat energy to said fluid.

9. The testing device of claim 8 wherein said heating means comprises at least one heating element peripherally disposed in said housing for the application of radiant heat energy therethrough and into contact with said fluid.

* * * * *